United States Patent
Kerz-Moehlendick et al.

(10) Patent No.: US 12,063,932 B2
(45) Date of Patent: *Aug. 20, 2024

(54) METHOD OF PROMOTING PLANT GROWTH EFFECTS

(71) Applicants: Bayer CropScience Aktiengesellschaft, Monheim am Rhein (DE); Bayer Aktiengesellschaft, Leverkusen (DE)

(72) Inventors: Friedrich Kerz-Moehlendick, Leverkusen (DE); Sybille Lamprecht, Leverkusen (DE); Klaus Tietjen, Langenfeld (DE)

(73) Assignees: BAYER CROPSCIENCE AKTIENGESELLSCHAFT, Monheim am Rhein (DE); BAYER AKTIENGESELLSCHAFT, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/852,788

(22) Filed: Jun. 29, 2022

(65) Prior Publication Data

US 2022/0346376 A1 Nov. 3, 2022

Related U.S. Application Data

(62) Division of application No. 16/462,028, filed as application No. PCT/EP2017/079786 on Nov. 20, 2017, now Pat. No. 11,419,334.

(30) Foreign Application Priority Data

Nov. 21, 2016 (EP) ..................... 16199902

(51) Int. Cl.
| | | |
|---|---|---|
| *A01N 43/40* | (2006.01) | |
| *A01P 3/00* | (2006.01) | |
| *A01P 21/00* | (2006.01) | |
| *C07D 213/79* | (2006.01) | |

(52) U.S. Cl.
CPC ........... *A01N 43/40* (2013.01); *C07D 213/79* (2013.01); *A01P 3/00* (2021.08); *A01P 21/00* (2021.08)

(58) Field of Classification Search
CPC ......... A01N 43/40; C07D 213/79; A01P 3/00; A01P 21/00
See application file for complete search history.

(56) References Cited

U.S. PATENT DOCUMENTS

| 4,367,336 A | 1/1983 | Nishiyama et al. |
| 4,995,902 A | 2/1991 | Brunner |
| 2013/0253018 A1 | 9/2013 | Hungenberg et al. |

FOREIGN PATENT DOCUMENTS

| EP | 0034917 A1 | 9/1981 |
| WO | 9942447 A1 | 8/1999 |
| WO | 2004016088 A2 | 2/2004 |
| WO | 2015121136 A1 | 8/2015 |

OTHER PUBLICATIONS

International Search Report of International Application No. PCT/EP2017/079786, mailed on Dec. 21, 2017.
EFSA: "Conclusion on pesticide peer review" EFSA Scientific Report, (2009) pp. 1-158.
Peng Wei et al., "Metabolic and Dynamic Profiling for Risk Assessment of Fluopyram, a Typical Phenylamide Fungicide Widely Applied in Vegetable Ecosystem" Scientific Report. vol. 6, (2016) p. 33898.
Anonymous, "Agronomy 317" Iowa State University. (Jul. 23, 2004) pp. 5-7.
Kelley, K. & Riechers, D.E., "Recent developments in auxin biology and new opportunities for auxinic herbicide research" Pesticide Biochemistry and Physiology, (2007) vol. 89, issue 1, pp. 1-11.
Kelley, K., et al., (2005). Soybean response to plant growth regulator herbicides is affected by other postemergence herbicides. Weed Science, 53(1), 101-112.
Sterling, T. & Hall, J.C., "Mechanism of Action of Natural Auxins and the Auxinic Herbicides" Herbicide Activity: Toxicology, Biochemistry and Molecular Biology, IOS Press, 1997.
Taiz, L. & Zeiger, E. (Eds.), Plant Physiology, Sinauer Association Inc., Sunderland, MA (2002) pp. 423-460.

*Primary Examiner* — John Pak
*Assistant Examiner* — Nathan W Schlientz
(74) *Attorney, Agent, or Firm* — Joseph Schuh (57) ABSTRACT

The present invention relates to the use of compound (A) according to formula (I) having the chemical name: 3-chloro-5-(trifluoromethyl)pyridine-2-carboxylic acid) for inducing positive growth responses in plants, a composition comprising compound (A) and a new method of plant treatment wherein is compound (A) applied to a plant, a plant part, plant propagation material or the habitat the plant is growing in to induce positive growth responses.

2 Claims, 3 Drawing Sheets
(3 of 3 Drawing Sheet(s) Filed in Color)

FIG. 2B 5 cm  Untreated Ctrl

FIG. 2C

FIG. 2D 1 ppm

FIG. 2E

FIG. 2F 80 ppm

FIG. 2G

FIG. 2H 420 ppm

METHOD OF PROMOTING PLANT GROWTH EFFECTS

CROSS-REFERENCE TO RELATED APPLICATIONS

This application is a Divisional of U.S. patent application Ser. No. 16/462,028, filed 17 May 2019, which is the National Stage entry of International Application No. PCT/EP2017/079786, filed 20 Nov. 2017, which claims priority to European Patent Application No. 16199902.4 filed 21 Nov. 2016. The disclosures of the priority applications are incorporated in their entirety herein by reference.

BACKGROUND

Field

The present invention relates to the use of compound (A) according to formula (I) having the chemical name: 3-chloro-5-(trifluoromethyl)pyridine-2-carboxylic acid) for inducing positive growth responses in plants, a composition comprising compound (A) and a new method of plant treatment wherein is compound (A) applied to a plant, a plant part, plant propagation material or the habitat the plant is growing in for promoting plant growth effects.

Description of Related Art

Plant development is regulated by a complex interaction between different plant hormones, eg. Auxins, cytokinins, abscisic acid, ethylene or gibberellins. As these hormones have a profound influence on plants, there have been significant efforts to use artificial plant hormones for plant growth regulation or as herbicides in agriculture. In particular Auxin was the first plant hormone to be discovered and is subject of decades long research (L. Taiz, E. Zeiger (Eds.), Plant Physiology, Sinauer Association Inc., Sunderland, MA (2002), pp. 423-460). The herbicidal effect of auxinic herbicides has been attributed to an overinduction of the auxin response in susceptible plants. While the concentration of natural auxin and its effects are tightly controlled under most circumstances, auxinic herbicides overcome the natural regulatory mechanisms of susceptible plants to cause an uncontrolled auxin response. At low doses, auxinic herbicides possess similar hormonal properties to natural auxin acting as plant growth promoters. With higher rates they cause various growth abnormalities in sensitive dicots, ranging from leaf epinasty and/or cupping and stem twisting, to thickening of stems and roots, and ultimately chlorosis and necrosis (Kelley and Riechers, Pesticide Biochemistry and Physiology, Vol 89, Issue 1, Pages 1-11; Sterling and Hall, Herbicide Activity: Toxicology, Biochemistry and Molecular Biology, IOS Press, Burke, VA (1997), pp. 111-141; Kelley et al., Weed Sci., 53 (2005), pp. 101-112). Auxins based on indole acetic acid in particular have been investigated due to their effects on cell elongation and division, root and bud formation. Synthetic auxins are used as herbicides as auxins in high application rates lead to uncontrolled growth and finally to the death of the plants. Indole-3-butryric acid on the other hand is used on plant cell culture to induce roots in cuttings or grafts. Auxins in higher concentrations lead not only to plant growth effects but can induce damages in plants due to unregulated growth phenomen in certain tissues. Therefore auxin and auxin like substances might be used as herbicides but also as growth promoter depending on their chemical structure and the concentration in which they are used. Chlorpyralid (3,6-dichloro-2-pyridinecarboxylic acid, CAS No 1702-17-6) is an example for an auxin-like compound where already in low concentrations damage is seen on the plant and it is therefore used as an herbicide.

Consequently it is an interest to provide simple chemical compounds which may promote plant growth effects over a relatively broad concentration range without showing the detrimental effect of a herbicide.

Compound (A) of the formula (I) having the chemical name 3-chloro-5-(trifluoromethyl)pyridine-2-carboxylic acid (I)

is known as an intermediate in the preparation of a range of pharmaceutically and agrochemically active substances, eg in WO-A 2015/121136. Compound (A) is commercially available under the CAS-No 80194-68-9.

There is an interest to provide further compounds of relatively simple chemical structure providing growth effects to plants at different stages of a plant lifetime.

SUMMARY

It is therefore an object of the present invention to provide a method for promoting plant growth effects.

The present invention describes the use of compound (A) according to formula (I)

(I)

having the chemical name: 3-chloro-5-(trifluoromethyl)pyridine-2-carboxylic acid) for inducing positive growth responses in plants, a composition comprising compound (A) and a method of plant treatment wherein is compound (A) applied to a plant, a plant part, plant propagation material or the habitat the plant is growing in to induce positive growth responses.

BRIEF DESCRIPTION OF THE DRAWINGS

The patent or application file contains at least one drawing executed in color. Copies of this patent or patent application with color drawing(s) will be provided by the Office upon request and payment of the necessary fee.

DETAILED DESCRIPTION OF A PREFERRED EMBODIMENT

Compound (A) used in the method of the present invention have been found to display a variety of plant growth promoting effect, depending upon the concentration used, the formulation employed and the type of plant species treated.

By virtue of the practice of the present invention a wide variety of plant growth promoting effects, including the following are defined, including but not limited to a) higher germination rates, b) an improved emergence and c) more vigorous seedlings.

In one embodiment a wide variety of plant growth promoting effects, including the following are defined, including but not limited to a) higher germination rates, b) an improved emergence, c) more vigorous seedlings and d) more flowers.

If, in the context of this description, the description refers to compound (A), this includes in each case all customary derivatives, such as the esters and salts, and isomers, in particular optical isomers, in particular the commercially available form or forms. Salts and esters are agronomically acceptable salts and esters. If compound (A) denotes an ester or salt, this in each case also comprises all other customary derivatives, such as other esters and salts, the free acids and neutral compounds, and isomers, in particular optical isomers, in particular the commercially available form or forms. The salts of compound (A) used in the context of the present invention may be used in the form of the respective alkali metal salts, alkaline earth salts or ammonium salts, preferably in the form of the respective alkali metal salts, more preferably in the form of the respective sodium or potassium salts, most preferably in the form of the respective sodium salts. In one embodiment the free acid of compound (A) is preferred.

The effect of compound (A) depends essentially on the time of application in relation to the developmental stage of the plant, and also on the amounts of compound (A) applied to the plants or their environment and on the type of application.

Growth regulating effects, may comprise earlier germination, better emergence, more developed root system and/or improved root growth, increased ability of tillering, more productive tillers, earlier flowering, increased plant height and/or biomass, shorting of stems, improvements in shoot growth, number of kernels/ear, number of ears/m$^2$, number of stolons and/or number of flowers, enhanced harvest index, bigger leaves, less dead basal leaves, improved phyllotaxy, earlier maturation/earlier fruit finish, homogenous riping, increased duration of grain filling, better fruit finish, bigger fruit/vegetable size, sprouting resistance and reduced lodging.

In another embodiment growth regulating effects, may comprise earlier germination, better emergence, more developed root system and/or improved root growth, increased ability of tillering, more productive tillers, earlier flowering, more flowers, increased plant height and/or biomass, shorting of stems, improvements in shoot growth, number of kernels/ear, number of ears/m$^2$, number of stolons and/or number of flowers, enhanced harvest index, bigger leaves, less dead basal leaves, improved phyllotaxy, earlier maturation/earlier fruit finish, homogenous riping, increased duration of grain filling, better fruit finish, bigger fruit/vegetable size, sprouting resistance and reduced lodging.

Increased or improved yield is referring to total biomass per hectare, yield per hectare, kernel/fruit weight, seed size and/or hectolitre weight as well as to improved product quality, comprising:

improved processability relating to size distribution (kernel, fruit, etc.), homogenous riping, grain moisture, better milling, better vinification, better brewing, increased juice yield, harvestability, digestibility, sedimentation value, falling number, pod stability, storage stability, improved fiber length/strength/uniformity, increase of milk and/or meet quality of silage fed animals, adaption to cooking and frying;

further comprising improved marketability relating to improved fruit/grain quality, size distribution (kernel, fruit, etc.), increased storage/shelf-life, firmness/softness, taste (aroma, texture, etc.), grade (size, shape, number of berries, etc.), number of berries/fruits per bunch, crispness, freshness, coverage with wax, frequency of physiological disorders, colour, etc.;

further comprising increased desired ingredients such as e.g. protein content, fatty acids, oil content, oil quality, aminoacid composition, sugar content, acid content (pH), sugar/acid ratio (Brix), polyphenols, starch content, nutritional quality, gluten content/index, energy content, taste, etc.;

and further comprising decreased undesired ingredients such as e.g. less mycotoxines, less aflatoxines, geosmin level, phenolic aromas, lacchase, polyphenol oxidases and peroxidases, nitrate content etc.

For example storage stability is defined as the time after the harvest of the crop in which the crop can be sold or consumed. This is of importance in particular for delicate and easily spoiled fruits like berries, eg strawberry, raspberry, blueberry, blackberry, gooseberry, red and black currant; stonefruit eg plum, cherry, apricot, peach, nectarine, mango, or other fruit eg persimmons.

Alternatively, growth regulators may also be used to promote vegetative growth. This is of great benefit when harvesting the vegetative plant parts. However, promoting vegetative growth may also promote generative growth in that more assimilates are formed, resulting in more or larger fruits.

Furthermore, beneficial effects on growth or yield may be achieved through improved nutrient use efficiency, especially nitrogen (N)-use efficiency, phosphorus (P)-use efficiency, water use efficiency, improved transpiration, respiration and/or $CO_2$ assimilation rate, better nodulation, improved Ca-metabolism etc.

Likewise, growth regulators may be used to alter the composition of the plants, which in turn may result in an improvement in quality of the harvested products. Under the influence of growth regulators, parthenocarpic fruits may be formed. In addition, it is possible to influence the sex of the flowers. It is also possible to produce sterile pollen, which is of great importance in the breeding and production of hybrid seed.

Furthermore, growth regulators may modulate plant senescence, which may result in prolonged green leaf area duration, a longer grain filling phase, improved yield quality, improved storage stability, etc.

Growth regulators may likewise be used to regulate fruit dehiscence. On the one hand, it may be possible to prevent premature fruit dehiscence. On the other hand, it is also possible to promote fruit dehiscence or even flower abortion to achieve a desired mass ("thinning"). In addition it may be possible to use growth regulators at the time of harvest to reduce the forces required to detach the fruits, in order to allow mechanical harvesting or to facilitate manual harvesting.

Growth regulators may also be used to achieve faster or else delayed ripening of the harvested material before or after harvest. This is particularly advantageous as it allows optimal adjustment to the requirements of the market. Moreover, growth regulators in some cases can improve the fruit colour. In addition, growth regulators can also be used to synchronize maturation within a certain period of time. This establishes the prerequisites for complete mechanical or manual harvesting in a single operation, for example in the case of tobacco, tomatoes or coffee.

By using growth regulators, it may be additionally possible to influence the resting of seed or buds of the plants, such that plants such as pineapple or ornamental plants in nurseries, for example, germinate, sprout or flower at a time when they are normally not inclined to do so. In areas where there is a risk of frost, it may be desirable to delay budding or germination of seeds with the aid of growth regulators, in order to avoid damage resulting from late frosts.

Finally, growth regulators may induce resistance of the plants to frost, drought or high salinity of the soil. This may allow the cultivation of plants in regions which are normally unsuitable for this purpose.

In one embodiment the amount of compound (A) applied may be sufficient to provide at least one plant growth promoting effect selected from the group consisting of: a) higher germination rates, b) an improved emergence and c) more vigorous seedlings.

In another embodiment the amount of compound (A) applied may be sufficient to provide at least one plant growth promoting effect selected from the group consisting of: a) higher germination rates, b) an improved emergence, c) more vigorous seedlings and d) more flowers.

Definitions:

a) Higher germination rates are defined as the percentage of germinated seeds from a seed population showing cotyledons after initial germination.

b) An improved emergence are defined as the percentage of seedlings emerging from the soil which have germinated from seeds which were covered by a 0.5 cm to 8 cm thick soil layer. Emergence is rated by visual inspection of the seedlings appearing from the soil.

c) More vigorous seedlings may be characterized by a variety of parameters like fresh weight, plant size, fresh root weight, size of cotyledons.

Seedlings are defined according to the BBCH scale to be in BBCH stage 00 to 10.

Flowers are defined to be the reproductive structure of flower plants (Angiosperms) according to the BBCH scale to be in BBCH stage 60 to 69.

All plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

Plants which can be treated in accordance with the invention include the following main crop plants: maize, soya bean, alfalfa, cotton, sunflower, *Brassica* oil seeds such as *Brassica napus* (e.g. canola, rapeseed), *Brassica rapa, B. juncea* (e.g. (field) mustard) and *Brassica carinata, Arecaceae* sp. (e.g. oilpalm, coconut), rice, wheat, sugar beet, sugar cane, oats, rye, barley, millet and sorghum, triticale, flax, nuts, grapes and vine and various fruit and vegetables from various botanic taxa, e.g. *Rosaceae* sp. (e.g. pome fruits such as apples and pears, but also stone fruits such as apricots, cherries, almonds, plums and peaches, and berry fruits such as strawberries, raspberries, red and black currant and gooseberry), *Ribesioidae* sp., *Juglandaceae* sp., *Betulaceae* sp., *Anacardiaceae* sp., *Fagaceae* sp., *Moraceae* sp., *Oleaceae* sp. (e.g. olive tree), *Actinidaceae* sp., *Lauraceae* sp. (e.g. avocado, cinnamon, camphor), *Musaceae* sp. (e.g. banana trees and plantations), *Rubiaceae* sp. (e.g. coffee), *Theaceae* sp. (e.g. tea), *Sterculiceae* sp., *Rutaceae* sp. (e.g. lemons, oranges, mandarins and grapefruit); *Solanaceae* sp. (e.g. tomatoes, potatoes, peppers, capsicum, aubergines, tobacco), *Liliaceae* sp., *Compositae* sp. (e.g. lettuce, artichokes and chicory—including root chicory, endive or common chicory), *Umbelliferae* sp. (e.g. carrots, parsley, celery and celeriac), *Cucurbitaceae* sp. (e.g. cucumbers—including gherkins, pumpkins, watermelons, calabashes and melons), *Alliaceae* sp. (e.g. leeks and onions), *Cruciferae* sp. (e.g. white cabbage, red cabbage, broccoli, cauliflower, Brussels sprouts, pak choi, kohlrabi, radishes, horseradish, cress and chinese cabbage), *Leguminosae* sp. (e.g. peanuts, peas, lentils and beans—e.g. common beans and broad beans), *Chenopodiaceae* sp. (e.g. Swiss chard, fodder beet, spinach, beetroot), *Linaceae* sp. (e.g. hemp), *Cannabeacea* sp. (e.g. cannabis), *Malvaceae* sp. (e.g. okra, cocoa), *Papaveraceae* (e.g. poppy), *Asparagaceae* (e.g. asparagus); useful plants and ornamental plants in the garden and woods including turf, lawn, grass and *Stevia rebaudiana*; and in each case genetically modified types of these plants.

Ornamental plants to be treated are aster, begonia, black-eyed Susan, bleeding heart, Chrysanthemum, Coneflower, Dahlia, daisy, carnation, petunia, geranium, hollyhock, impatiens, lobelia, malva, morning glory, marigold, periwinkle, primrose, ranunculus, roses, snapdragon, sunflower, tansy, tulip, violet, zinnia.

Preferred ornamentals are roses.

Preferred plants to be treated are soybean, corn, cotton, oilseeds, in particular winter or spring oilseed rape, canola, vegetables, in particular those of the Solanaceae family like tomatoes, potatoes, peppers, capsicum, aubergines, tobacco, rice, wheat, in particular spring wheat, winter wheat, Durum, oats, rye, barley, millet and sorghum, triticale, berries, eg strawberry, raspberry, blueberry, blackberry, gooseberry, red and black currant; stonefruit eg plum, cherry, apricot, peach, nectarine, mango, or other fruit eg persimmons.

As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts" or "parts of plants" or "plant parts" have been explained above. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They can be cultivars, varieties, bio- or genotypes.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology, RNA interference—RNAi-technology or microRNA—miRNA-technology). A heterologous gene that is located in the genome is also called a transgene. A transgene that is defined by its particular location in the plant genome is called a transformation or transgenic event.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content and composition for example cotton or starch, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance.

Plants or plant cultivars (obtained by plant biotechnology methods such as genetic engineering) which may also be treated according to the invention show altered quantity, quality and/or storage-stability of the harvested product and/or altered properties of specific ingredients of the harvested product.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics.

Plants or plant cultivars (that can be obtained by plant biotechnology methods such as genetic engineering) which may also be treated according to the invention are plants, such as oilseed rape or related Brassica plants, with altered oil profile characteristics. Such plants can be obtained by genetic transformation, or by selection of plants contain a mutation imparting such altered oil profile characteristics.

Plants or plant cultivars (that can be obtained by plant biotechnology methods such as genetic engineering) which may also be treated according to the invention are plants, such as oilseed rape or related Brassica plants, with altered seed shattering characteristics. Such plants can be obtained by genetic transformation, or by selection of plants contain a mutation imparting such altered seed shattering characteristics and include plants such as oilseed rape plants with delayed or reduced seed shattering.

Plants or plant cultivars (that can be obtained by plant biotechnology methods such as genetic engineering) which may also be treated according to the invention are plants, such as Tobacco plants, with altered post-translational protein modification patterns.

The application rates of the compounds I are from 0.005 to 1 kg/ha, preferably 0.01 to 0.8 kg/ha, in particular 0.02 to 0.7 kg/ha, very particularly 0.02 to 0.5 kg/ha.

Formulations

The present invention further relates to a composition for inducing positive growth responses in plants, comprising compound (A). These are preferably compositions which comprise agriculturally suitable auxiliaries, solvents, carriers, surfactants or extenders.

A carrier is a natural or synthetic, organic or inorganic substance with which the active ingredients are mixed or combined for better applicability, in particular for application to plants or plant parts or seed. The carrier, which may be solid or liquid, is generally inert and should be suitable for use in agriculture.

Useful solid carriers include: for example ammonium salts and natural rock flours, such as kaolins, clays, talc, chalk, quartz, attapulgite, montmorillonite or diatomaceous earth, and synthetic rock flours, such as finely divided silica, alumina and silicates; useful solid carriers for granules include: for example, crushed and fractionated natural rocks such as calcite, marble, pumice, sepiolite and dolomite, and also synthetic granules of inorganic and organic flours, and granules of organic material such as paper, sawdust, coconut shells, maize cobs and tobacco stalks; useful emulsifiers and/or foam-formers include: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Additionally suitable are oligo- or polymers, for example those derived from vinylic monomers, from acrylic acid, from EO and/or PO alone or in combination with, for example, (poly)alcohols or (poly)amines. It is also possible to use lignin and its sulphonic acid derivatives, unmodified and modified celluloses, aromatic and/or aliphatic sulphonic acids and also their adducts with formaldehyde.

Compound (A) may be converted to the customary formulations, such as solutions, emulsions, wettable powders, water- and oil-based suspensions, powders, dusts, pastes, soluble powders, soluble granules, granules for broadcasting, suspoemulsion concentrates, natural products impregnated with active ingredient, synthetic substances impregnated with active ingredient, fertilizers and also microencapsulations in polymeric substances.

Compound (A) may be applied as such, in the form of their formulations or the use forms prepared therefrom, such as ready-to-use solutions, emulsions, water- or oil-based suspensions, powders, wettable powders, pastes, soluble powders, dusts, soluble granules, granules for broadcasting, suspoemulsion concentrates, natural products impregnated with active ingredient, synthetic substances impregnated with active ingredient, fertilizers and also microencapsulations in polymeric substances. Application is accomplished in a customary manner, for example by watering, spraying, atomizing, broadcasting, dusting, foaming, spreading-on and the like. It is also possible to deploy Compound (A) may by the ultra-low volume method or to inject Compound (A) itself into the soil. It is also possible to treat the seed of the plants.

The formulations mentioned may be prepared in a manner known per se, for example by mixing Compound (A) with at least one customary extender, solvent or diluent, emulsifier, dispersant and/or binder or fixing agent, wetting agent, a water repellent, if appropriate siccatives and UV stabilizers and if appropriate dyes and pigments, antifoams, preservatives, secondary thickeners, stickers, gibberellins and also other processing auxiliaries.

In one embodiment not only formulations are included which are already ready for use and can be deployed with a suitable apparatus to the plant or the seed, but also commercial concentrates which have to be diluted with water prior to use.

Compound (A) may be present as such or in their (commercial) formulations and in the use forms prepared from these formulations as a mixture with other (known) active ingredients, such as insecticides, attractants, sterilants, bactericides, acaricides, nematicides, fungicides, growth regulators, herbicides, fertilizers, safeners and/or semiochemicals.

The auxiliaries used may be those substances which are suitable for imparting particular properties to the composition itself or and/or to preparations derived therefrom (for example spray liquors, seed dressings), such as certain technical properties and/or also particular biological properties. Typical auxiliaries include: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

Liquefied gaseous extenders or carriers are understood to mean liquids which are gaseous at standard temperature and under standard pressure, for example aerosol propellants such as halohydrocarbons, or else butane, propane, nitrogen and carbon dioxide.

In the formulations it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids. Further additives may be mineral and vegetable oils.

If the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Compositions comprising compound (A) may additionally comprise further components, for example surfactants. Suitable surfactants are emulsifiers and/or foam formers, dispersants or wetting agents having ionic or nonionic properties, or mixtures of these surfactants. Examples thereof are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is necessary if Compound (A) and/or one of the inert carriers is insoluble in water and when application is effected in water. The proportion of surfactants is between 5 and 40 per cent by weight of the inventive composition.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Further additives may be perfumes, mineral or vegetable, optionally modified oils, waxes and nutrients (including trace nutrients), such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability.

If appropriate, other additional components may also be present, for example protective colloids, binders, adhesives, thickeners, thixotropic substances, penetrants, stabilizers, sequestering agents, complex formers. In general, the active ingredients can be combined with any solid or liquid additive commonly used for formulation purposes.

The formulations contain generally between 0.05 and 99% by weight, 0.01 and 98% by weight, preferably between 0.1 and 95% by weight, more preferably between 0.5 and 90% of active ingredient, most preferably between 10 and 70 per cent by weight.

The formulations described above can be used for inducing positive growth responses, in which the compositions comprising compound (A) are applied to the plants and/or in their habitat.

Mixtures

Compound (A) may be used as such or in formulations thereof and may be mixed with known fungicides, bactericides, acaricides, nematicides or insecticides.

In one embodiment a composition comprises compound (A) and at least one other agrochemically active ingredient comprising a pyridyl.

In one embodiment a composition comprises compound (A) and at least one other agrochemically active ingredient being Fluopyram or Fluopicolide.

In one embodiment a composition comprises compound (A) and Fluopyram.

In one embodiment a composition comprises compound (A) and Fluopicolide.

In one embodiment compound (A) may be mixed in tank mixes with other agrochemically active ingredients comprising a pyridyl.

In one embodiment compound (A) may be mixed in tank mixes with Fluopyram or Fluopicolide.

In one embodiment compound (A) may be applied sequentially with other agrochemically active ingredients comprising a pyridyl.

In one embodiment compound (A) may be applied sequentially with Fluopyram or Fluopicolide.

In one embodiment compound (A) may be applied sequentially with Fluopyram.

In one embodiment compound (A) may be applied sequentially with Fluopicolide.

Fluopyram is known from WO-A 2004/16088, Fluopicolide is known from WO-A 99/42447.

Useful mixing partners include, for example, known fungicides, insecticides, acaricides, nematicides or else bactericides (see also Pesticide Manual, 14th ed.).

A mixture with other known active ingredients, such as herbicides, or with fertilizers and growth regulators, safeners and/or semiochemicals, is also possible.

Seed Treatment

The invention furthermore includes a method for treating seed.

A further aspect of the present invention relates in particular to seeds (dormant, primed, pregerminated or even with emerged roots and leaves) treated with compound (A). The inventive seeds are used in methods for inducing positive growth responses in seeds and emerged plants from the seeds. In these methods, seed treated with compound (A).

Compound (A) may also be suitable for the treatment of seeds and young seedlings. The roots and shoots of the growing plant are particularly sensitive to compounds inducing growth responses. Accordingly, there is great interest in inducing positive growth responses in the seed and the germinating plant by using appropriate compositions.

Compound (A) may also be suitable for the treatment of flowering buds and flowers. The flowering buds are particularly sensitive to compounds inducing growth responses. Accordingly, there is great interest in inducing positive growth responses in the flowering buds and flowers by using appropriate compositions.

It is also desirable to optimize the amount of compound (A) used so as to provide the best possible growth response for the seeds, the germinating plants and emerged seedlings, but without damaging the plants themselves by compound (A) used. In particular, methods for the treatment of seed should also take into consideration the intrinsic phenotypes of transgenic plants in order to achieve optimum protection of the seed and the germinating plant.

It is also desirable to optimize the amount of compound (A) used so as to provide the best possible growth response for the seeds, the germinating plants and emerged seedlings as well as the flowering buds and the flowers, but without damaging the plants themselves by compound (A) used. In particular, methods for the treatment of seed should also take into consideration the intrinsic phenotypes of transgenic plants in order to achieve optimum protection of the seed and the germinating plant.

In one embodiment a method for inducing positive growth responses in seeds, germinating plants and emerged seedlings is described by treating the seeds with an inventive composition. The invention also relates to the use of the compositions for treating seeds for inducing positive growth responses in the seeds, the germinating plants and emerged seedlings. The invention further relates to seeds which has been treated with a composition comprising compound (A) for inducing positive growth responses.

In another embodiment a method for inducing positive growth responses in seeds, germinating plants, emerged seedlings, flowering buds and flowers is described by treating the seeds with an inventive composition. The invention also relates to the use of the compositions for treating seeds for inducing positive growth responses in the seeds, the germinating plants emerged seedlings, flowering buds and flowers. The invention further relates to flowers which has been treated with a composition comprising compound (A) for inducing positive growth responses.

One of the advantages of the present invention is that the treatment of the seeds with these compositions not only may induce positive growth responses in the seed itself, but also may induce positive growth responses in the resulting plants after emergence. In this way, the immediate treatment of the crop at the time of sowing or shortly thereafter protect plants as well as seed treatment in prior to sowing. It is likewise considered to be advantageous that compound (A) or compositions comprising compound (A) may be used especially also for transgenic seed, in which case the plant which grows from this seed is capable of expressing a protein which acts against pests, herbicidal damage or abiotic stress.

Compound (A) may be suitable for inducing positive growth responses in seed of any plant variety which is used in agriculture, in the greenhouse, in forests or in horticulture. More particularly, the seed is that of cereals (such as wheat, barley, rye, millet and oats), oilseed rape, maize, cotton, soybeen, rice, potatoes, sunflower, beans, coffee, beet (e.g. sugar beet and fodder beet), peanut, vegetables (such as tomato, cucumber, onions and lettuce), lawns and ornamental plants. Of particular significance is the treatment of the seed of wheat, soybean, oilseed rape, maize and rice. Of very particular significance is the treatment of the seed of wheat, soybean, oilseed rape, maize and rice and roses.

As also described below, the treatment of transgenic seed with compound (A) may be of particular significance. This refers to the seed of plants containing at least one heterologous gene which allows the expression of a polypeptide or protein, e.g. having insecticidal properties. These heterologous genes in transgenic seeds may originate, for example, from microorganisms of the species *Bacillus, Rhizobium, Pseudomonas, Serratia, Trichoderma, Clavibacter, Glomus* or *Gliocladium*. These heterologous genes preferably originates from *Bacillus* sp., in which case the gene product is effective against the European corn borer and/or the Western corn rootworm. Particularly preferably, the heterologous genes originate from *Bacillus thuringiensis*.

The composition is applied to seeds either alone or in a suitable formulation. Preferably, the seed is treated in a state in which it is sufficiently stable for no damage to occur in the course of treatment. In general, seeds can be treated at any time between harvest and some time after sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again, or seeds just after priming, or seeds stored in primed conditions or pre-germinated seeds, or seeds sown on nursery trays, tapes or paper.

When treating the seeds, it generally has to be ensured that the amount of the composition applied to the seed and/or the amount of further additives is selected such that the germination of the seed is not impaired, or that the resulting plant is not damaged.

Compound (A) may be applied directly, i.e. without containing any other components and without having been diluted. In general, it is preferable to apply the compositions to the seed in the form of a suitable formulation. Suitable formulations and methods for seed treatment are known to those skilled in the art. Compound (A) may be converted to the customary formulations relevant to on-seed applications, such as solutions, emulsions, suspensions, powders, foams, slurries or combined with other coating compositions for seed, such as film forming materials, pelleting materials, fine iron or other metal powders, granules, coating material for inactivated seeds, and also ULV formulations.

These formulations are prepared in a known manner, by mixing compound (A) with customary additives, for example customary extenders and solvents or diluents, dyes, wetting agents, dispersants, emulsifiers, antifoams, preservatives, secondary thickeners, adhesives, gibberellins, and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients including plant growth regulators. Usable with preference are alkylnaphthalenesulphonates, such as diisopropyl- or diisobutylnaphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients including plant growth regulators. Usable with preference are nonionic or anionic dispersants or mixtures of nonionic or anionic dispersants. Useful nonionic dispersants include especially ethylene oxide/propylene oxide block polymers, alkylphenol polyglycol ethers and tristryrylphenol polyglycol ether, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The formulations for on-seed applications usable in accordance with the invention can be used to treat a wide variety of different kinds of seed either directly or after prior dilution with water. For instance, the concentrates or the preparations obtainable therefrom by dilution with water can be used to dress the seed of cereals, such as wheat, barley, rye, oats, and triticale, and also seeds of maize, soybean, rice, oilseed rape, peas, beans, cotton, sunflowers, and beets, or else a wide variety of different vegetable seeds. The formulations usable in accordance with the invention, or the dilute preparations thereof, can also be used for seeds of transgenic plants.

For treatment of seeds with the formulations usable in accordance with the invention, or the preparations prepared therefrom by adding water, all mixing units usable customarily for on-seed applications are useful. Specifically, the procedure in on-seed applications is to place the seeds into a mixer, to add the particular desired amount of the formulations, either as such or after prior dilution with water, and to mix everything until all applied formulations are distributed homogeneously on the seeds. If appropriate, this is followed by a drying operation.

The application rate of the formulations usable in accordance with the invention can be varied within a relatively wide range. It is guided by the particular content of the active ingredients in the formulations and by the seeds For seed treatment, the application rates of the mixture are generally from 0.001 to 250 g/100 kg of seed, preferably 0.01 to 100 g/100 kg of seed, more preferably 0.1 to 50 g/100 kg of seed, even more preferably 0.1 to 2 g/100 kg of seed.

The precise amount of compound (A) will depend upon the particular plant species being treated. This may be determined by the man skilled in the art with a few experiments and may vary in plant responses depending upon the total amount of compound used, as well as the particular plant species, which is being treated. Of course, the amount of compound (A) should be non-phytotoxic with respect of the plant being treated.

Although the preferred method of application of the compound (A) used in the process of this invention is directly to the foliage and stems or other parts of the plants, it as been deemed that such compounds may be applied to the soil in which the plants are growing, and that such compounds will be root-absorbed to a sufficient extent so as to result in plant responses in accordance with the teachings of this invention.

The following examples are illustrative of methods of plant growth regulation according to the invention, but should not be understood as limiting the said instant invention.

Example A

Soybean seeds of the variety Merlin were treated with 1.2, 0.6 and 0.3 g of compound (A) per 100 kg seeds. Compound (A) was provided as an aqueous solution with a concentration of 1000 ppm compound (A). The treated seeds were seeded into soil/quartz in five replicates at the same day. Germination was observed four days later. Plant height, fresh and dry weight of stem and roots were determined after 19 days.

TABLE 1

| Treatment | Rate [g/100 kg seeds] | Plant height [% of untreated control] | Fresh weight plant [g] | Fresh weight stem [g] | Fresh weight roots [g] | Dry weight stem [g] | Dry weight roots [g] |
| --- | --- | --- | --- | --- | --- | --- | --- |
| Untreated control | — | 100 | 2.53 | 100 | 100 | 100 | 100 |
| Cpd (A) | 1.2 | 87 | 2.24 | 88 | 69 | 77 | 68 |
| Cpd (A) | 0.6 | 103 | 2.53 | 100 | 107 | 107 | 108 |
| Cpd (A) | 0.3 | 111 | 2.62 | 103 | 106 | 114 | 105 |

Example B

Soybean seeds of the variety Merlin were treated with 1.2, 0.6 and 0.3 g of compound (A) per 100 kg seeds. Compound (A) was provided as an aqueous solution with a concentration of 1000 ppm compound (A). The treated seeds were seeded into soil/quartz in five replicates at the same day. Germination was observed four days later. Root volume was determined after 19 days.

TABLE 2

| Treatment | Rate [g/100 kg seeds] | Root volume [cm$^3$] |
| --- | --- | --- |
| Untreated control | — | 0.82 |
| Cpd (A) | 1.2 | 0.50 |
| Cpd (A) | 0.6 | 0.96 |
| Cpd (A) | 0.3 | 0.83 |

Example C

Soybean seeds of the variety Merlin were treated with 1.2, 0.6 and 0.3 g of compound (A) per 100 kg seeds. Compound (A) was provided as an aqueous solution with a concentration of 1000 ppm compound (A). The treated seeds were seeded into soil/quartz in five replicates at the same day. Germination was observed four days later. Comparative photographs were taken after 19 days.

Figure 1A:
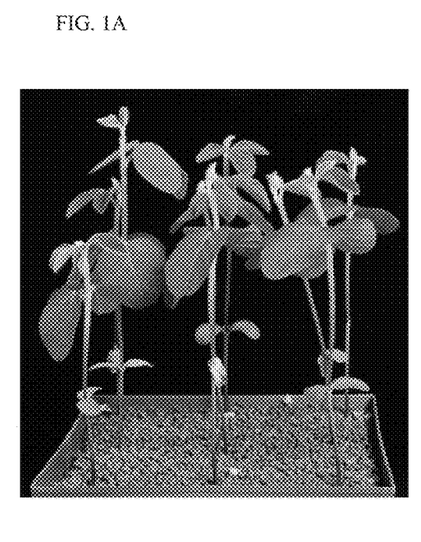
FIGS. 1A-1H. Soybean seeds of the variety Merlin were untreated FIG. 1A (top view) and FIG. 1B (side view), or treated 1.2 g/100 kg/seeds of Compound (A) in FIG. 1C (top view) and FIG. 1D (side view); or treated with 0.6 g/100 kg seeds of Compound (A) in FIG. 1E (Lop view) and FIG. 1F (side view); or treated with 0.3 g/100 kg seeds of compound (A) in FIG. 1G (top view) and FIG. 1H (side view). Seedlings were evaluated after 19 days.
Figure 1B:
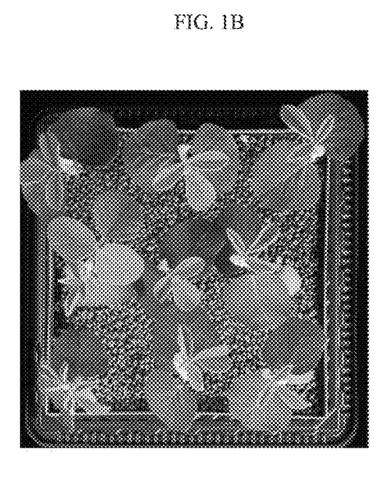
Figure 1C:
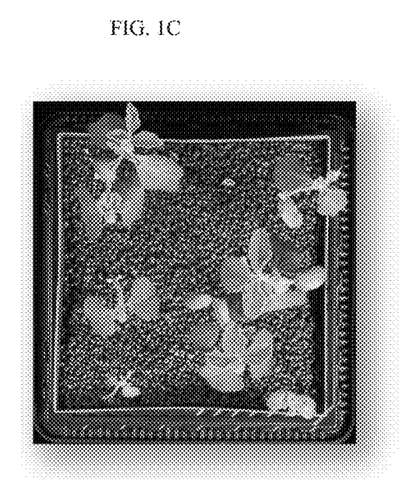
Figure 1D:
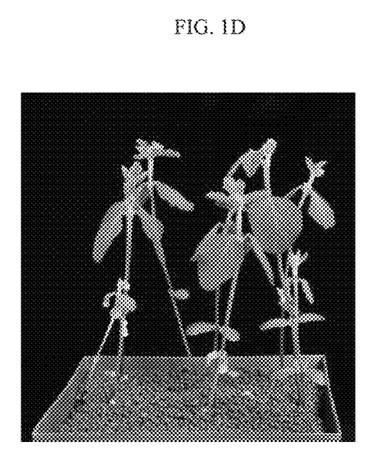
Figure 1E:
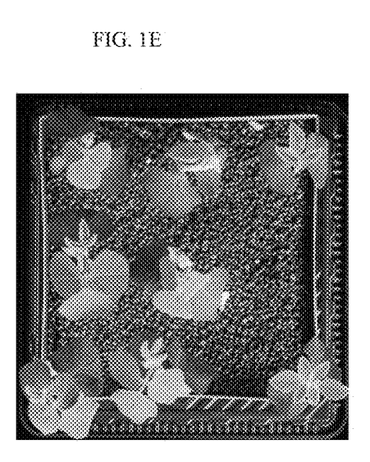
Figure 1F:
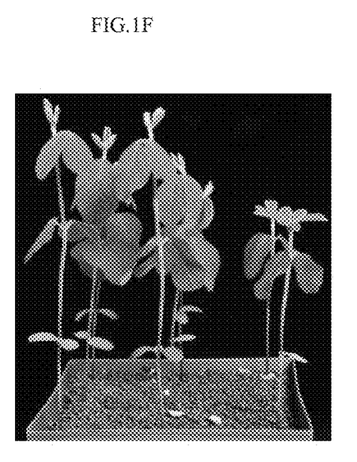
Figure 1G:
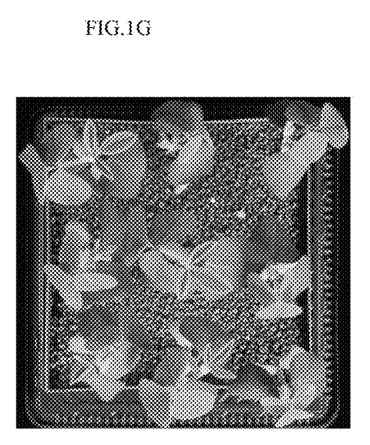
Figure 1H:
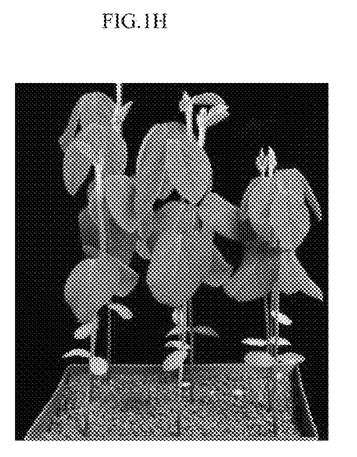

FIGS. 1E and 1F (side view) (0.6 g/100 kg seeds of Compound (A)) and FIGS. 1G and 1H (0.3 g/100 kg seeds of compound (A)) show a higher growth of the seedlings and an increased biomass of leaves in comparison to the untreated control (FIGS. 1A and 1B).

Example D

Roses of the variety Kordana Mixkar were cultivated in 2 litre pots in soil in the greenhouse at 23 degree Celsius and 80% humidity. Compound (A) and Clopyralid as a comparison were applied as a foliar application on 2016-05-25 at application rates according to the following table 3 Ammonium sulfate and methylated soybean oil were used as penetration enhancing agents.

TABLE 3

| Number | Compound | Active ingredient [ppm] | Volume of active ingredient solution [ml] | Volume of water [ml] |
|---|---|---|---|---|
| 1 | Untreated control | | | 50 |
| 2 | Untreated control + ammonium sulfate + methylated soybean oil | | | 50 |
| 3 | Compound (A) | 850 | 42.5 | 7.5 |
| 4 | | 420 | 21 | 29 |
| 5 | | 250 | 12.5 | 37.5 |
| 6 | | 170 | 8.5 | 41.5 |
| 7 | | 80 | 4 | 46 |
| 8 | | 40 | 2 | 48 |
| 9 | | 20 | 1 | 49 |
| 10 | | 10 | 0.5 | 49.5 |
| 11 | | 1 | 0.05 | 49.95 |

Figure 2A:
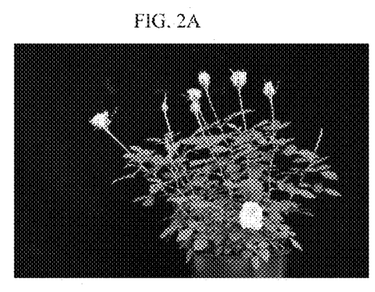
FIGS. 2A-2H. Rose plants of the variety Kordana Mixkar were treated in five replicates. Untreated control is shown in FIG. 2A (side view) and FIG. 2B (top view). Treatment at 1 ppm is shown in FIG. 2C (side view) and FIG. 2D (top view). Treatment at 80 ppm is shown in FIG. 2E (side view) and FIG. 2F (top view). Treatment at 420 ppm is showing in FIG. 2G (side view) and FIG. 2H (top view). Rose plants were evaluated for quantity and fullness of flowers.
Figure 2B:
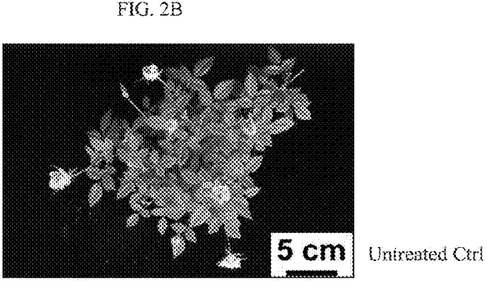
Figure 2C:
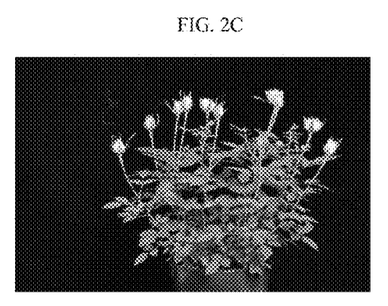
Figure 2D:
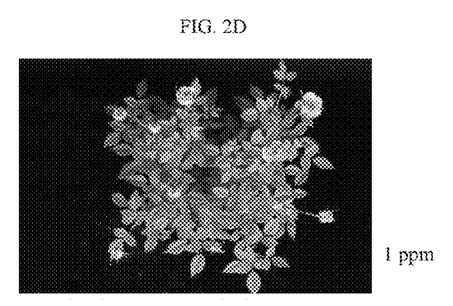
Figure 2E:
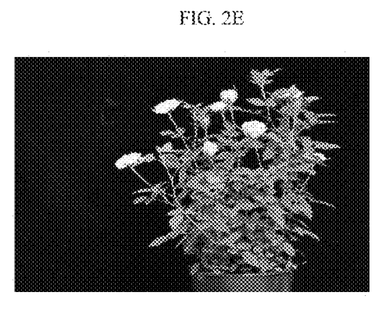
Figure 2F:
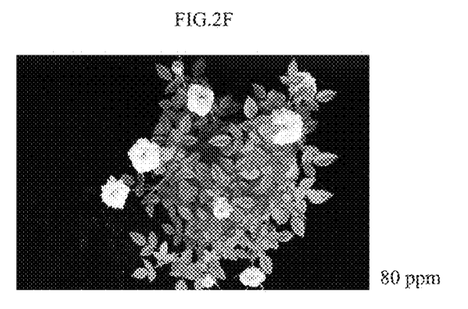
Figure 2G:
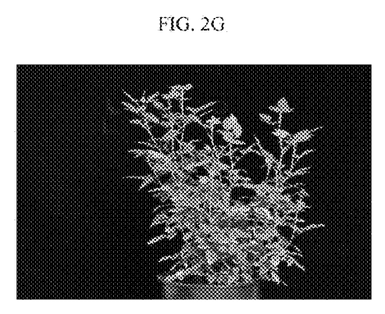
Figure 2H:
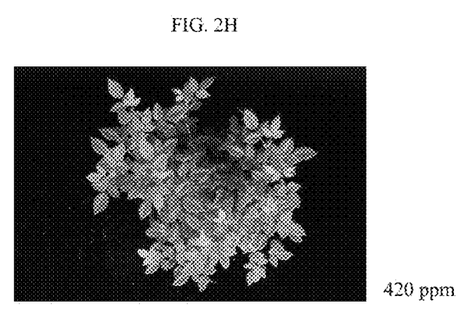

Rose plants were treated in five replicates. The number of flowers was assessed by visual inspection on 2016-06-14. FIGS. 2C-2H show that the rose plants developed more and fuller flowers than the untreated controls (FIG. 2A-2B) up to a concentration of Compound (A) of 80 ppm.

TABLE 4

| Nr. | Sample | Conc [ppm] | No Flowers A | B | C | D | E | Average (A to E) |
|---|---|---|---|---|---|---|---|---|
| 1 | Untreated control | 0 | 10 | 9 | 8 | 10 | 10 | 9.4 |
| 2 | Untreated control + ammonium sulfate + methylated soybean oil | 0 | 10 | 10 | 12 | 9 | 10 | 10.2 |
| 3 | Compound (A) | 850 | 2 | 3 | 10 | 5 | 6 | 5.2 |
| 4 | | 420 | 8 | 7 | 3 | 4 | 3 | 5 |
| 5 | | 250 | 3 | 9 | 3 | 4 | 8 | 5.4 |
| 6 | | 170 | 8 | 10 | 10 | 5 | 11 | 8.8 |
| 7 | | 80 | 12 | 13 | 11 | 11 | 10 | 11.4 |
| 8 | | 40 | 11 | 8 | 13 | 12 | 12 | 11.2 |
| 9 | | 20 | 11 | 10 | 12 | 10 | 10 | 10.6 |
| 10 | | 10 | 11 | 10 | 10 | 10 | 10 | 10.2 |
| 11 | | 1 | 8 | 7 | 11 | 10 | 12 | 9.6 |

The invention claimed is:

1. An agrochemical composition comprising compound (A) according to formula (I)

and fluopicolide.

2. An agrochemical composition comprising compound (A) according to formula (I)

and fluopyram.

* * * * *

UNITED STATES PATENT AND TRADEMARK OFFICE
CERTIFICATE OF CORRECTION

PATENT NO. : 12,063,932 B2
APPLICATION NO. : 17/852788
DATED : August 20, 2024
INVENTOR(S) : Kerz-Moehlendick et al.

It is certified that error appears in the above-identified patent and that said Letters Patent is hereby corrected as shown below:

On the Title Page

Item (57), under "ABSTRACT", in Column 2, Line 3, delete "acid)" and insert -- acid --, therefor.

In the Specification

In Column 1, Line 21, delete "acid)" and insert -- acid --, therefor.
In Column 2, Line 1, delete "Chlorpyralid" and insert -- Clopyralid --, therefor.
In Column 2, Line 51, delete "acid)" and insert -- acid --, therefor.
In Column 3, Line 1, delete "(Lop view)" and insert -- (top view) --, therefor.
In Column 4, Line 41, delete "mycotoxines," and insert -- mycotoxins, --, therefor.
In Column 4, Line 41, delete "aflatoxines," and insert -- aflatoxins, --, therefor.
In Column 4, Line 42, delete "lacchase," and insert -- laccase, --, therefor.
In Column 6, Line 31, delete "Actinidaceae" and insert -- Actinidiaceae --, therefor.
In Column 6, Line 34, delete "Sterculiceae" and insert -- Sterculiaceae --, therefor.
In Column 6, Line 48, delete "Cannabeacea" and insert -- Cannabaceae --, therefor.
In Column 13, Line 31, delete "soybeen," and insert -- soybean, --, therefor.
In Column 14, Line 45, delete "tristryrylphenol" and insert -- tristyrylphenol --, therefor.
In Column 16, Line 65, delete "3" and insert -- 3. --, therefor.

Signed and Sealed this
Twelfth Day of November, 2024

Katherine Kelly Vidal
*Director of the United States Patent and Trademark Office*